(12) United States Patent
Bayly

(10) Patent No.: US 9,433,769 B2
(45) Date of Patent: Sep. 6, 2016

(54) LINE SEPARATION PROTECTOR

(71) Applicant: FRESENIUS MEDICAL CARE HOLDINGS, INC., Waltham, MA (US)

(72) Inventor: Michelle Bayly, Abington, MA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 0 days.

(21) Appl. No.: 14/103,525

(22) Filed: Dec. 11, 2013

(65) Prior Publication Data

US 2015/0157845 A1  Jun. 11, 2015

(51) Int. Cl.
| | | |
|---|---|---|
| F16L 13/04 | (2006.01) | |
| A61M 39/10 | (2006.01) | |
| A61M 25/02 | (2006.01) | |
| A61M 39/08 | (2006.01) | |

(52) U.S. Cl.
CPC .......... *A61M 39/10* (2013.01); *A61M 39/1011* (2013.01); *A61M 39/08* (2013.01); *A61M 2025/028* (2013.01); *A61M 2039/1016* (2013.01); *Y10T 29/49826* (2015.01)

(58) Field of Classification Search
USPC .................. 285/114–116, 320, 414, 1, 80
See application file for complete search history.

(56) References Cited

U.S. PATENT DOCUMENTS

| | | | | |
|---|---|---|---|---|
| 1,989,823 A | * | 2/1935 | Raabe ........................... | 439/370 |
| 3,469,864 A | * | 9/1969 | Guerrero ....................... | 285/308 |
| 4,068,870 A | * | 1/1978 | Whitney et al. .............. | 285/320 |
| 4,183,603 A | * | 1/1980 | Donarummo ................. | 439/369 |
| 4,333,505 A | * | 6/1982 | Jones et al. ................... | 141/383 |
| 4,946,455 A | | 8/1990 | Rosen | |
| D313,277 S | | 12/1990 | Haining | |
| 4,997,421 A | * | 3/1991 | Palsrok et al. ................ | 604/174 |
| 5,139,289 A | * | 8/1992 | Koss .............................. | 285/80 |
| 5,248,306 A | * | 9/1993 | Clark et al. ................... | 604/537 |
| 5,350,201 A | * | 9/1994 | Bynum .......................... | 285/92 |
| 5,423,775 A | * | 6/1995 | Cannon ......................... | 604/533 |
| 5,536,258 A | | 7/1996 | Folden | |
| 5,766,032 A | * | 6/1998 | LaPointe et al. ............. | 439/371 |
| 5,782,808 A | | 7/1998 | Folden | |
| 6,070,491 A | * | 6/2000 | Claudio et al. ................ | 74/546 |
| 6,076,424 A | * | 6/2000 | McMurtrey et al. ........... | 74/544 |
| 6,354,521 B1 | * | 3/2002 | Kusilek et al. ................ | 239/600 |
| 6,375,231 B1 | * | 4/2002 | Picha et al. ................... | 285/114 |
| 6,612,619 B2 | * | 9/2003 | Wieder .......................... | 285/23 |

(Continued)

OTHER PUBLICATIONS

Pogorelc "Catheter infection startup thinks it's found an overlooked source of contamination in IV tube connector," MEDCITY News (Sep. 13, 2012).

(Continued)

*Primary Examiner* — Aaron Dunwoody
(74) *Attorney, Agent, or Firm* — Kilyk & Bowersox, P.L.L.C.

(57) ABSTRACT

A line separation protector is provided that can include an arm, an anchor, a clasp attached to the arm, and a tab connected to and configured to manipulate the clasp. A tubing subsystem is also provided that can include a first tubing threaded through the anchor of the line separation protector described herein. A line connection system is also provided and can include the tubing subsystem described herein, and a second tubing, wherein the clasp of the line separation protector is configured to engage the second tubing. A method of protecting a line connection system is also described herein and includes engaging a second tubing with the clasp of the protector to form a protected line connection system.

21 Claims, 6 Drawing Sheets

(56) References Cited

U.S. PATENT DOCUMENTS

| | | |
|---|---|---|
| 6,722,705 B2 | 4/2004 | Korkor |
| 6,783,520 B1 | 8/2004 | Candray et al. |
| 7,331,613 B2 | 2/2008 | Schulte |
| 7,509,956 B2 * | 3/2009 | Dombrowski ............ 128/202.27 |
| 7,614,123 B2 * | 11/2009 | Schweikert ..................... 24/522 |
| 7,758,082 B2 | 7/2010 | Weigel et al. |
| D621,077 S * | 8/2010 | Fleischman ..................... D26/9 |
| 7,980,598 B2 * | 7/2011 | Tsubota et al. ................. 285/80 |
| 8,042,838 B2 | 10/2011 | Buckler et al. |
| 2014/0035273 A1 | 2/2014 | Schnell et al. |

OTHER PUBLICATIONS

"HemoSafe™ Patient Connector Clip for Hemodialysis," Fresenius USA, Catalog No. 04-9100-1 (Printed Sep. 24, 2013).

\* cited by examiner

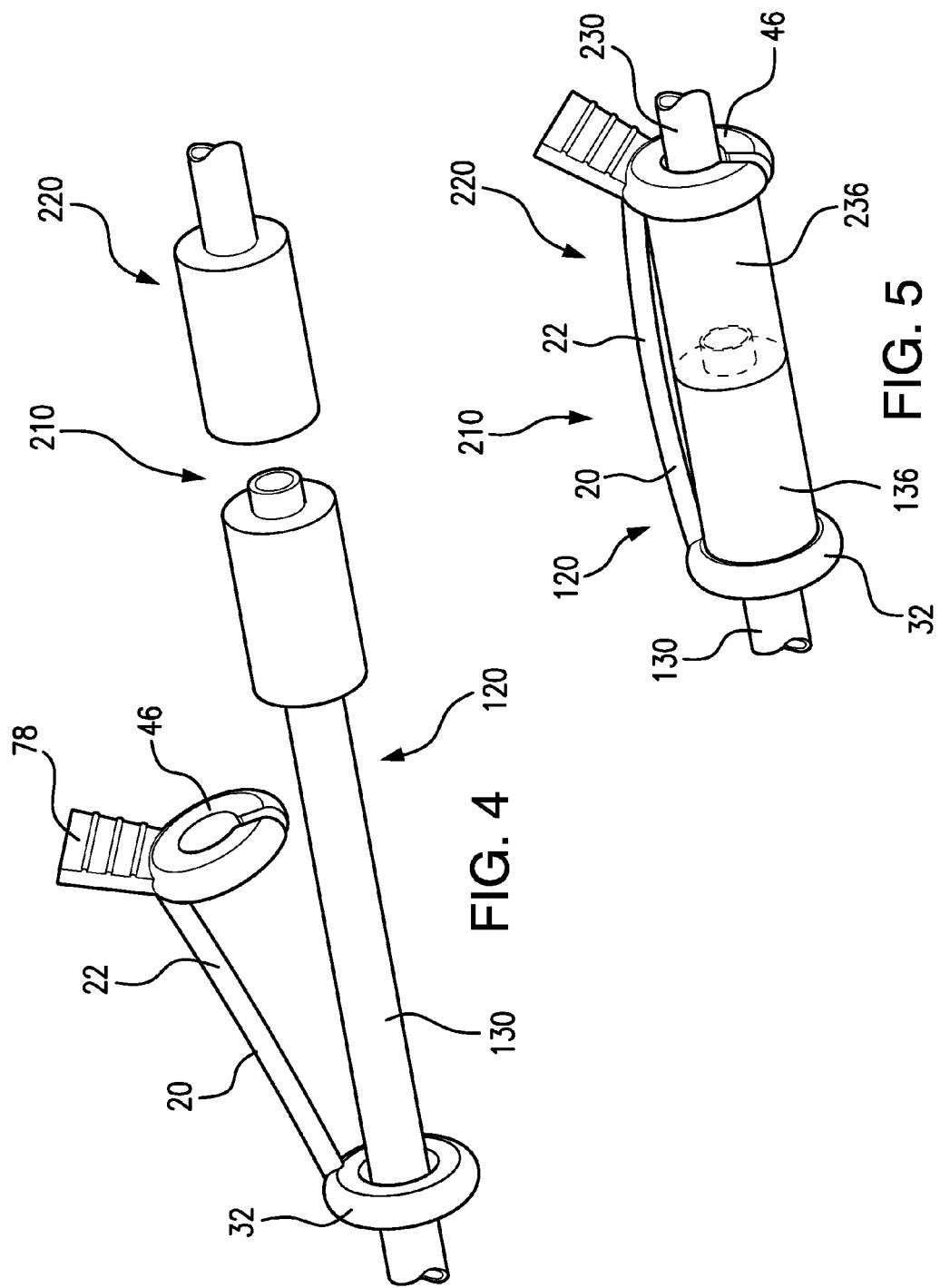

LINE SEPARATION PROTECTOR

FIELD OF THE INVENTION

This invention relates to line separation protectors, as well as to systems and method using the same, for preventing disengagement of fluid lines in dialysis and other contexts.

BACKGROUND OF THE INVENTION

When blood is removed from a patient for apheresis, phlebotomy, dialysis, transfusion, diagnostics, and other applications, the blood often first passes through a catheter attached to vasculature of the patient and then to a blood tubing line. The catheter and blood tubing line can be connected together by a variety of mechanisms, such as a luer lock. While a luer lock or alternative connector generally provides a secure fitting, a risk of inadvertent disengagement remains and can cause undesired consequences. To help minimize that risk, devices have been developed to provide a level of redundancy to the line connection should the primary connector become disconnected, loose, or otherwise fail. For example, U.S. Pat. No. 6,783,520 B1 describes a connector holding device to prevent accidental disconnection between complementary halves of a fluid connection device. The device has a pair of semi-cylindrical clips for partially surrounding a tube. The arms are mounted on an arm having notches along its length that allows adjustment of the spacing between the two clips. These notches, however, can act as teeth and can cause discomfort to the patient as they rub against the patient's arm or other body part. This device can also completely detach from a tubing set and become misplaced during packaging or use. Other approaches for securing a fluid connection device utilize an adhesive tape; however, doing so leaves adhesive residue that can cause needlestick or skin irritation. Accordingly, there exists a need for a line separation protector that minimizes discomfort to the patient, reduces the chance for misplacement, is capable of both quick engagement and quick release, and provides a secure connection between two coupled lines.

SUMMARY OF THE INVENTION

It is a feature of the present invention to provide a line separation protector to prevent disengagement of fluid lines that are coupled together.

It is a further feature of the present invention to provide a line separation protector to prevent disengagement of blood lines during a blood treatment procedure, thus helping to prevent blood leaks and blood contamination.

Another feature of the present invention is to provide a line separation protector that minimizes discomfort to the patient, reduces the chance for misplacement, and is capable of both quick engagement and quick release.

A further feature of the present invention is to provide subsystems, systems, and methods utilizing the line separation protector.

Additional features and advantages of the present invention will be set forth in part in the description that follows, and in part will be apparent from the description, or can be learned by practice of the present invention. The objectives and other advantages of the present invention will be realized and attained by means of the elements and combinations particularly pointed out in the present description and appended claims.

To achieve these and other features of the present invention, the present invention provides a line separation protector that can include an arm, an anchor, a clasp, and a tab. The arm can include a first end, a second end, an inner surface, and an outer surface. The anchor can be proximal to and intersect with the first end of the arm. The anchor can also have an inner circumferential surface defining an inner circumference, an inner lateral surface, an outer lateral surface, and an outer circumferential surface defining an outer circumference. The clasp can be proximal to and intersect with the second end of the arm and can extend from the inner surface of the arm. The clasp can be pliant. The clasp can include first and second hooks. The first hook can extend from the arm and can include a distal tip, an inner circumferential surface, an outer circumferential surface, an inner lateral surface, and an outer lateral surface. The second hook can extend from the arm and include a distal tip, an inner surface, an outer surface, an inner lateral surface, and an outer lateral surface. The first hook can arc toward the distal tip of the second hook and the second hook can arc toward the distal tip of the first hook. Accordingly, the distal tips of the first and second hooks can curve towards each other and be separated by a gap in the clasp. The inner circumferential surfaces of the first and second hooks can define an inner circumference of the clasp. The tab can be proximal to and intersect with the second end of the arm and can extend away from the outer surface of the arm.

A tubing subsystem is also provided by the present invention. The tubing subsystem can include a first tubing and the line separation protector as described herein. The first tubing can include a first end and a second end. The first tubing can also include an intermediate section and a connector section. The intermediate section can be located between the first and second ends of the first tubing and can include an outer circumferential surface defining a first outer circumference or outer diameter. The connector section can be located adjacent to and intersecting the intermediate section, proximal to the first end of the first tubing. The connector section can include a second outer circumference or outer diameter that is larger than the first outer circumference or outer diameter. The connector section has an outer surface that is adjacent to the outer surface of the intermediate section, but which has an outer diameter that is larger than the outer diameter of the intermediate section. The anchor can have an inner diameter that is larger than the outer diameter of the intermediate section yet smaller than the outer diameter of the connector section. The anchor can thus encircle and slide along the intermediate section but cannot slide over and past the connector section.

A line connection system is further provided by the present invention that can include the tubing subsystem described herein and a second tubing subsystem including a second tubing. The second tubing can include a first end and a second end. The second tubing can also include an intermediate section and a connector section. The intermediate section can be located between the first and second ends and can have an outer circumferential surface that can be, for example, of the same size and shape as the outer circumferential surface of the intermediate section of the first tubing. The connector section of the second tubing can be located adjacent to and intersecting the intermediate section of the second tubing and proximal to the first end of the second tubing. The connector section of the second tubing can have an outer circumference defined by an outer diameter that is larger than the outer diameter of the intermediate section. The clasp of the line separation protector can engage the intermediate section of the second tubing.

The clasp can have an inner diameter that is larger than the outer diameter of the intermediate section of the second tubing. The inner diameter of the clasp can be smaller than the outer diameter of the connector section of the second tubing such that the connector section cannot slip through the clasp.

A method of protecting a line connection system as described herein is also provided by the present invention. The method can include coupling a connector of a first tubing bearing the line separation protector with a complementary connector engaging the intermediate section of the second tubing with the clasp to form a protected coupling between the two tubings, which is protected from disconnection. The method can also include disengaging the clasp from the intermediate section of the second tubing to disconnect the coupling. The engaging, the disengaging, or both, can comprise gripping or otherwise manipulating the tab.

It is to be understood that both the foregoing general description and the following detailed description are exemplary and explanatory only and are intended to provide a further explanation of the present invention, without limiting the invention.

BRIEF DESCRIPTION OF THE DRAWINGS

The invention may be more fully understood with reference to the accompanying drawings. The drawings are intended to illustrate, not limit, the present teachings.

FIG. 4 is a perspective view of the line connection system shown in FIG. 2, but wherein the clasp of the line separation protector has been detached from the first tubing that carries the protector.

FIG. 5 is a perspective view of the line connection system shown in FIGS. 2-4, but wherein the clasp of the line separation protector is in a secured position clasping an intermediate section of the second tubing and wherein the first and second tubings are in a connected or coupled configuration.

DETAILED DESCRIPTION OF THE INVENTION

Figure 1A:
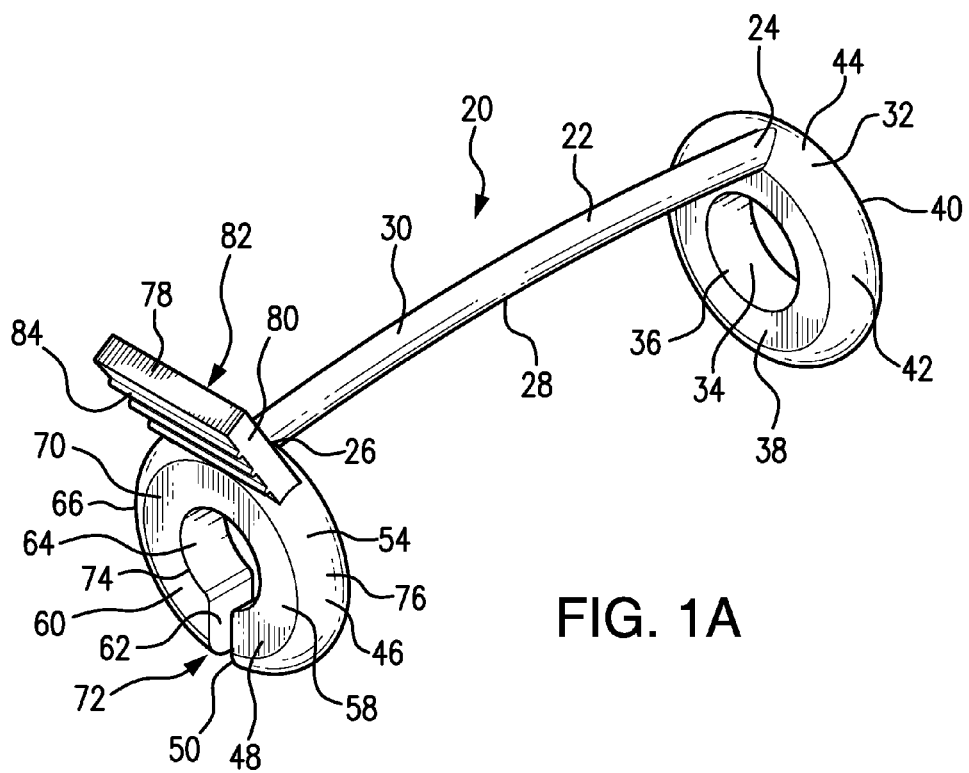
FIG. 1A is a front, top perspective view of a line separation protector in accordance with the present invention.

A line separation protector is provided by the present invention and includes an arm, an anchor, a clasp, and a tab. The arm can include a first end, a second end, an inner surface, and an outer surface. The anchor can be ring-shaped or donut-shaped and can have a through hole. The anchor can be provided proximal to and intersecting with the first end and can extend from the arm in a direction that is substantially perpendicular to a direction of elongation of the arm and to the inner surface of the arm. The anchor can have an inner circumferential surface defining an inner circumference, an inner lateral surface, an outer lateral surface, and an outer circumferential surface defining an outer circumference. The clasp can be substantially donut-shaped or substantially ring-shaped with the exception of a gap along the ring. The clasp can include a through hole. The clasp can be located proximal to and intersecting with the second end of the arm and can extend from the arm in a direction that is substantially perpendicular to the direction of elongation of the arm and to the inner surface of the arm. The clasp can be pliant. The clasp can include first and second hooks. The first hook can extend from the arm and can include a distal tip, an inner circumferential surface, an outer circumferential surface, an inner lateral surface, and an outer lateral surface. The second hook can extend from the arm and can include a distal tip, an inner surface, an outer surface, an inner lateral surface, and an outer lateral surface. The first hook can arc toward the distal tip of the second hook and the second hook can arc toward the distal tip of the first hook. The distal tips of the first and second hooks can approach each other but not contact each other and thus define a gap in the otherwise ring-shaped clasp. The inner circumferential surface of the first hook can oppose the inner circumferential surface of the second hook, and the two inner circumferential surfaces can mirror one another. The inner circumferential surfaces of the first and second hooks can define an inner circumference of the clasp. Similarly, the outer circumferential surfaces of the first and second hooks can define an outer circumference of the clasp. The tab can be proximal to and intersect with the second end of the arm and can extend from the outer surface of the arm in a direction away from the clasp. The tab can include opposing faces. The tab can include a tab edge, a first lateral surface adjacent the tab edge, and a second lateral surface adjacent the tab edge, and facing away from the first lateral surface.

In addition to the clasp, other parts of the line separation protector can be formed from a pliant material, or the entirety of the line separation protector can comprise a pliant material. For example, the arm can also be pliant. The clasp need not be entirely pliant but at least one of the two hooks can be pliant, bendable, flexible, and/or elastically deformable. Hinges can be provided as part of the clasp. All or part of each hook can be pliant.

The clasp, the arm, the anchor, the tab, or any part thereof, or combination thereof, can be pliant and can comprise a rubber, elastomeric, bendable, resilient, flexible, and/or plastic material. The pliant material can be elastic, pliable, flexible, deformable, elastically deformable, or any combination thereof. The pliant material can comprise a plastic, a polymer, an elastomer, a rubber, a shape-memory material, a metal, an alloy, a memory alloy, or any combination thereof. Any suitable pliant material can be used. Examples of suitable pliant materials include, but are not limited to, those described in the Encyclopedia of Plastics, Polymers, And Resins (Chemical Publishing Co., 1983), Concise Encyclopedia of Plastics (Springer, 2000), Rosato's Plastics Encyclopedia and Dictionary (Hanser Gardner, 1993), and Encyclopedic Dictionary of Polymers (Springer, 2011). While non-pliant or rigid materials can be used for one or more parts of the line separation protector, their use can be minimized so as to reduce potential discomfort to the patient. Both pliant and non-pliant materials can be used to provide the line separation protector with sufficient structural integrity while at the same time providing sufficient pliability for ease of manipulation, and softness for patient comfort.

The geometry of all or part of the line separation protector can be varied to adjust function, resistance to detachment, and to account for variations in the diameter of tubing, couplings, and other related components with which the line separation protector engages. For example, the inner circumference of the anchor can define an inner diameter that can be smaller than, equal to, or larger than an inner diameter of the clasp. The inner circumference (and/or diameter) of the anchor can be slightly larger than the outer circumference or outer diameter of the tubing onto which the anchor of the line separation protector is to be slid or threaded. The inner circumference of the anchor can alternatively be substantially the same as the outer diameter of the tubing onto which the anchor of the protector is mounted such that the protector does not easily slide along the length of the tubing. The through hole of the anchor can be in-line with, that is, aligned with, the through hole of the clasp. The inner lateral surface of the anchor can be substantially parallel to the inner lateral surfaces of the first and second hooks. Reference to substantially parallel or substantially perpendicular herein includes the capability of achieving an angle from parallelism or perpendicularity of less than 25°, less than 20°, less than 15°, less than 10°, less than 5.0°, less than 1.0°, less than 0.1°, or any intervening angle or range. Herein, substantially parallel can also mean parallel and substantially perpendicular can also mean perpendicular. Greater variability is also allowed given the use of pliant material that can allow bending, torsion, and the like, of the line separation protector.

The size of the gap between the distal tips of the first and second hooks can be selected based on the degree of control desired and based on the desired ease of removal and/or tightness of fit of the clasp from or onto a particular tubing. For example, relative to an otherwise entire 360° ring-shape of the clasp, the gap can have an arc length of less than about 180°, less than about 150°, less than about 120°, less than about 90°, less than about 60°, less than about 30°, less than about 20°, less than about 10°, or any intervening angle or range. Reference to circumferences can also include perimeters, for example, where a full or partial rectilinear geometry of a tubing or other component makes it desirable to configure complementary perimetal shapes.

A tubing subsystem is also provided by the present invention. The tubing subsystem can include a first tubing and the line separation protector described herein. The first tubing can include a first end and a second end. The first tubing can also include on intermediate section and a connector section. The intermediate section can be located between the first end and the second end. The intermediate section can have an outer diameter. The connector section can be located adjacent to and intersecting with the intermediate section, proximal to the first end. The connector section can haven an outer diameter that is larger than the outer diameter of the intermediate section. The anchor can surround or encircle the intermediate section of the first tubing. The anchor can comprise a closed ring that completely encircles the intermediate section so that the line separation protector does not become separated or misplaced; however, a slight gap, split, or perforation can be provide if complete removability of the line protection connector is desired or preferred. The anchor can have an inner diameter that can be smaller than the outer diameter of the connector section and larger than or equal to the outer diameter of the intermediate section. The connector section can include a first half of a luer lock. The first half of the luer lock can be a male luer connector or a female luer connector.

A disposable blood tubing set that includes the tubing subsystem described herein is also provided. In such a disposable blood tubing set, the first tubing can be, or can include, a blood line. Although blood lines are exemplified herein, the line separation protector and systems and methods using the same can be used for connecting many other types of tubing and conduits, including water lines, intravenous fluid lines, gas lines, and the like.

A line connection system is provided by the present invention, which can include the tubing subsystem described herein and a second tubing subsystem including a second tubing. The second tubing can include a first end and a second end. The second tubing can also include an intermediate section and a connector section. The intermediate section can be located between the first end and the second end, and can have an outer surface defining an outer circumference, and an outer diameter. The connector section can be located adjacent to and intersecting with the intermediate section and proximal to the first end. The connector section can have an outer circumferential surface defining an outer circumference, and an outer diameter. The connector section can have an outer diameter that is larger than the outer diameter of the intermediate section. The inner diameter of the clasp can be smaller than the outer diameter of the connector section. The first and second tubing subsections can be configured to be joined together to enable a leak-free fluid communication between the first tubing and the second tubing.

In an exemplary line connection system, the anchor of the line separator protector can be on, or encircling, the intermediate section of the first tubing, and the clasp can be either engaged with or disengaged from the intermediate section of the second tubing. The engagement and/or disengagement can be complete or partial. Due to the pliable nature of the pliant clasp, the geometry of the clasp, such as its circumference, can vary and need not be exact, depending on its positioning and the desired degree of engagement and/or disengagement. When fully engaged, the clasp can surround the intermediate section of the second tubing with the exception of the gap between the distal tips of the first and second hooks. The inner diameter of the clasp can be smaller than, larger than, or equal to, the outer diameter of the intermediate section of the second tubing. For example, the inner diameter of the clasp can be less than or equal to the outer diameter of the intermediate section of the second tubing, and, after engaging the intermediate section of the second tubing, can be equal to or about equal to the outer diameter of the intermediate section of the second tubing.

The geometry of the arm can vary, including its length, depending on whether the clasp is engaged or disengaged, especially given the use of pliant materials. For example, the arm can have an arm length as measured from the inner lateral surface of the anchor to the inner lateral surfaces of the first and second hooks. The connector section on the first tubing can have a first connector length that can exclude the length of any male connector overhang, and the connector section of the second tubing can have a second connector length. The connector sections of the first and second tubings, when joined together, can define a connector length. The connector length can be the sum of the first and second connector lengths, and the arm length can be longer than, slightly shorter than, equal to, or about equal to, the connector length.

When engaged, the spatial relationship between the line separation protector and the components of the first and second tubings is generally tighter than when disengaged. While a tight or snug fit can be achieved, the spacing and/or friction can be sufficiently loose so as to enable the line separation protector to be rotated and/or easily disengaged. When the line separation protector is in use, i.e., engaged, the inner lateral surface of the anchor can be in contact with the outer lateral surface of the connector section of the first tubing. The inner lateral surfaces of the first and second hooks can be in contact with the outer lateral surface of the connector section of the second tubing. The inner surface of the arm can be in contact with the outer surfaces of the first and second connector sections. The connector section of the second tubing can include a second half of a luer lock. The second half of the luer lock can comprise a female luer connector, for example, to complement a male luer connector on the connector section of the first tubing. While the location of the male and female halves of the luer lock connector can be switched, the convention in the art is to have the male luer connector on the first tubing when the first tubing is a blood line, and the female luer connector on the second tubing when the second tubing is a catheter or needle access line. Like the first tubing, the second tubing can independently comprise or be a blood line, a fluid line, a gas line, a catheter line, a needle access line, a combination thereof, or the like.

A method of protecting a line connection between two lines that are coupled together is also described herein and provided by the present invention. The method can include coupling together a first tubing and a second tubing and then engaging an intermediate section of the second tubing with the clasp of a line separation protector as described herein. As a result, a line connection system is formed that is protected against separation. One or more additional steps can be performed prior to the engaging. For example, the method can include sliding the anchor along an intermediate section of the first tubing until the inner lateral surface of the anchor contacts the outer lateral surface of the connector section of the first tubing. For example, the method can include first joining together first and second connector sections to enable a fluid communication between first and second tubings, and then sliding the protector into place. The clasp can then be engaged to an intermediate section of the second tubing. Such additional steps can be reversed beginning with disengaging the clasp. Accordingly, the method can also include disengaging the clasp from the intermediate section of the second tubing. The engaging, the disengaging, or both, can involve gripping or manipulating the tab. For example, the tab can be pushed when engaging the clasp and pulled when disengaging the clasp.

Various modifications can be made to the line separation protectors, subsystems, systems, and/or method without departing from the scope of the present invention. For example, the anchor can also be provided with a gap in its circumference. Such an anchor gap can be small in size, relative to the size of the gap separating the hooks of the clasp, so that the anchor does not disengage as easily as the clasp. If the anchor disengages too easily the entire line separation protector can become lost or misplaced. A second tab can also be provided proximal to the first end of the arm to aid in movement and/or removal of the anchor. The tab and/or second tab can be provided with a general roughness, grading, ribs, ridges, bumps, depressions, protrusions, and the like, to increase friction, which allows the tab to be gripped or contacted more easily. The angle of the tab with respect to the arm can also be varied, for example, from perpendicular, to slanting toward the first end, to slanting away from the first end. For example, the angle of the tab to the arm can be about 170°, about 150°, about 120°, about 110°, about 100°, about 90°, about 80°, about 70°, about 60°, about 30°, about 20°, or any intervening angle or range. The shape of the arm, anchor, and/or clasp can be varied. For example, the components can be fully rounded so that adjacent surfaces are continuous, or partially rounded or beveled so that edges are rounded but lateral sides are relatively planar. Cross-sectional shapes described as circular or round can instead be elliptical in shape, can be otherwise curvilinear, can have square cross-sections, can have rectilinear cross-sections, can comprise a combination thereof, or the like.

With reference to the drawing figures, FIG. 1A is a front, top perspective view of a line separation protector 20 in accordance with the present invention. Line separation protector 20 includes an arm 22. Arm 22 has a first end 24, a second end 26, an inner surface 28, and an outer surface 30. An anchor 32 is located proximal to and intersecting with first end 24 and extends from arm 22 and substantially perpendicular to inner surface 28. Anchor 32 includes an inner circumferential surface 34 defining an inner circumference 36, which, due to the circular geometry of the anchor, can be described as an inner diameter. Anchor 32 further includes an inner lateral surface 38, an outer lateral surface 40, and an outer circumferential surface 42 defining an outer circumference 44 such that anchor 32 has an outer diameter. A pliant clasp 46 is located proximal to and intersecting with second end 26. Clasp 46 extends from arm 22 substantially perpendicular to inner surface 28. Clasp 46 includes a first hook 48 extending away from arm 22. First hook 48 has a distal tip 50, an inner circumferential surface 52 (see FIG. 1G), an outer circumferential surface 54, an inner lateral surface 56 (see FIG. 1G), and an outer lateral surface 58. Clasp 46 also includes a second hook 60 extending away from arm 22. Second hook 60 includes a distal tip 62, an inner circumferential surface 64, an outer circumferential surface 66, an inner lateral surface 68 (see FIGS. 1C and 1G), and an outer lateral surface 70. First hook 48 arcs toward distal tip 62 of second hook 60. Second hook 60 arcs toward distal tip 50 of first hook 48. A gap 72 is defined between distal tips 50 and 62. Inner circumferential surface 52 of first hook 48 opposes (faces) inner circumferential surface 64 of second hook 60, and together they define an inner circumference 74 of clasp 46. Similarly, outer circumferential surfaces 54 and 66 define an outer circumference 76 of clasp 46. A tab 78 is located proximal to and intersecting with second end 26 of arm 22 and extends away from outer surface 30 of arm 22 at an angle relative to the outer circumferential surfaces 54 and 66 of first and second hooks 48 and 60, respectively. Tab 78 includes a tab edge 80, a first tab lateral surface 82 adjacent tab edge 80, and a second tab lateral surface 84 also adjacent tab edge 80 and facing away from first tab lateral surface 82.

Figure 1B:
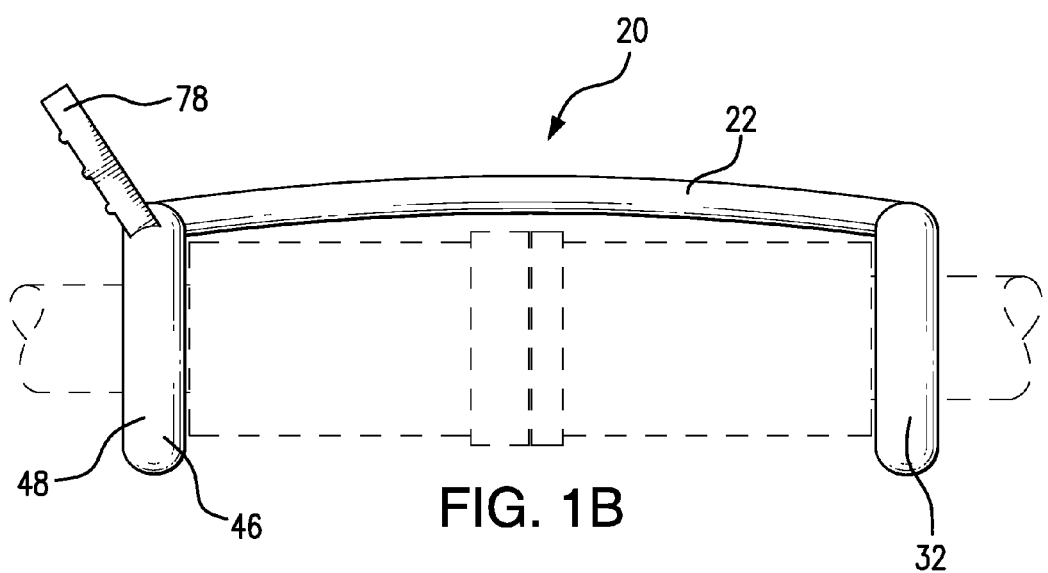
FIG. 1B is a right side view of the line separation protector shown in FIG. 1A.

FIG. 1B is a right side, side view of line separation protector 20 of FIG. 1A in operable engagement with a tubing connection that is shown in phantom. Clasp 46 and anchor 32 border and contact respective ends of the tubing connection such that line separation protector 20 straddles the connected connector sections. Tab 78 extends from clasp 46 up and away from arm 22 at an angle of about 110° with respect to arm 22.

Figure 1C:
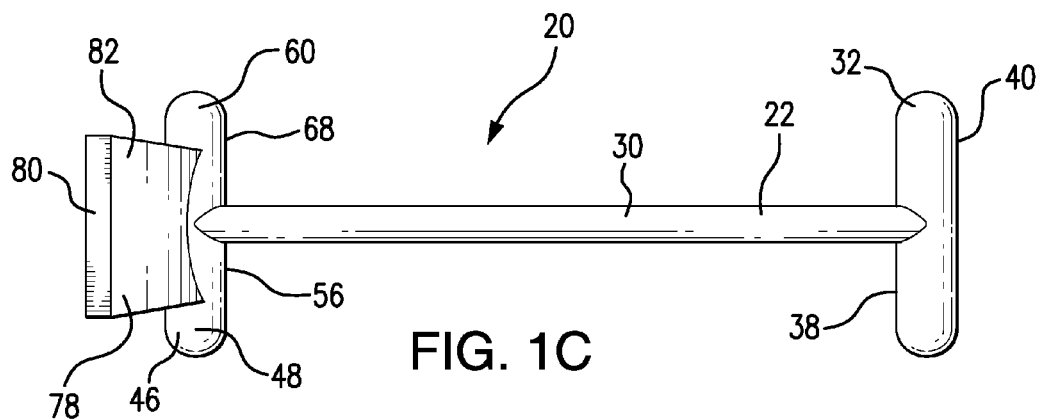
FIG. 1C is a top, plan view of the line separation protector shown in FIG. 1A.

FIG. 1C is a top, plan view of line separation protector 20. Outer surface 30 of arm 22 is visible. Lateral surface 82 of tab 78 is visible intersecting with tab edge 80. First and second hooks 48 and 60 of clasp 46 extend from opposite sides of arm 22, at the end of arm 22 that is opposite anchor 32. Outer lateral surface 40 and inner lateral surface 38 of anchor 32 can be seen on opposing faces of anchor 32. Inner lateral surface 38 of anchor 32 faces inner lateral surface 56 of first hook 48 and faces inner lateral surface 68 of second hook 60.

Figure 1D:
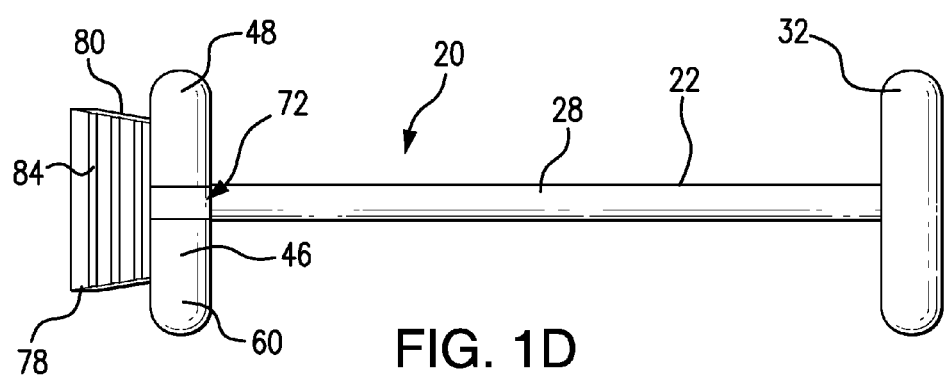
FIG. 1D is a bottom view of the line separation protector shown in FIG. 1A.

FIG. 1D is a bottom view of line separation protector 20, wherein inner surface 28 of arm 22 is visible. Arm 22 extends from anchor 32 to clasp 46. First hook 48 and second hook 60 of clasp 46 arc toward and end at gap 72. Tabs 78 extends from clasp 46 and lateral surface 84 and tab edge 80, of tab 78, are visible.

Figure 1E:
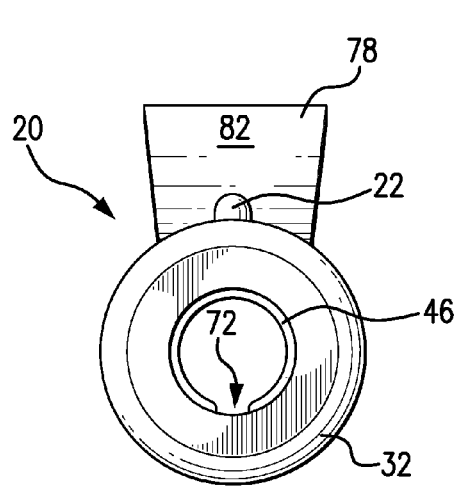
FIG. 1E is a rear end view of the line separation protector shown in FIG. 1A.
Figure 1F:
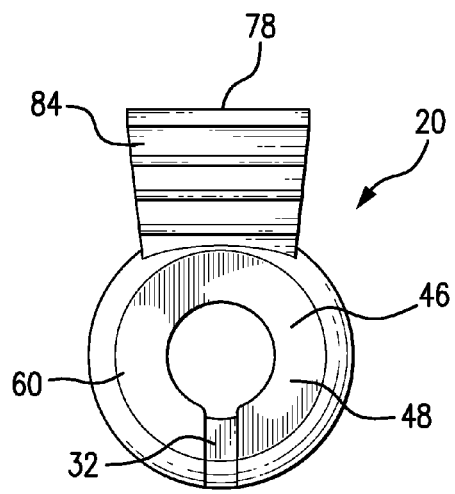
FIG. 1F is a front end view of the line separation protector shown in FIG. 1A.
Figure 1G:
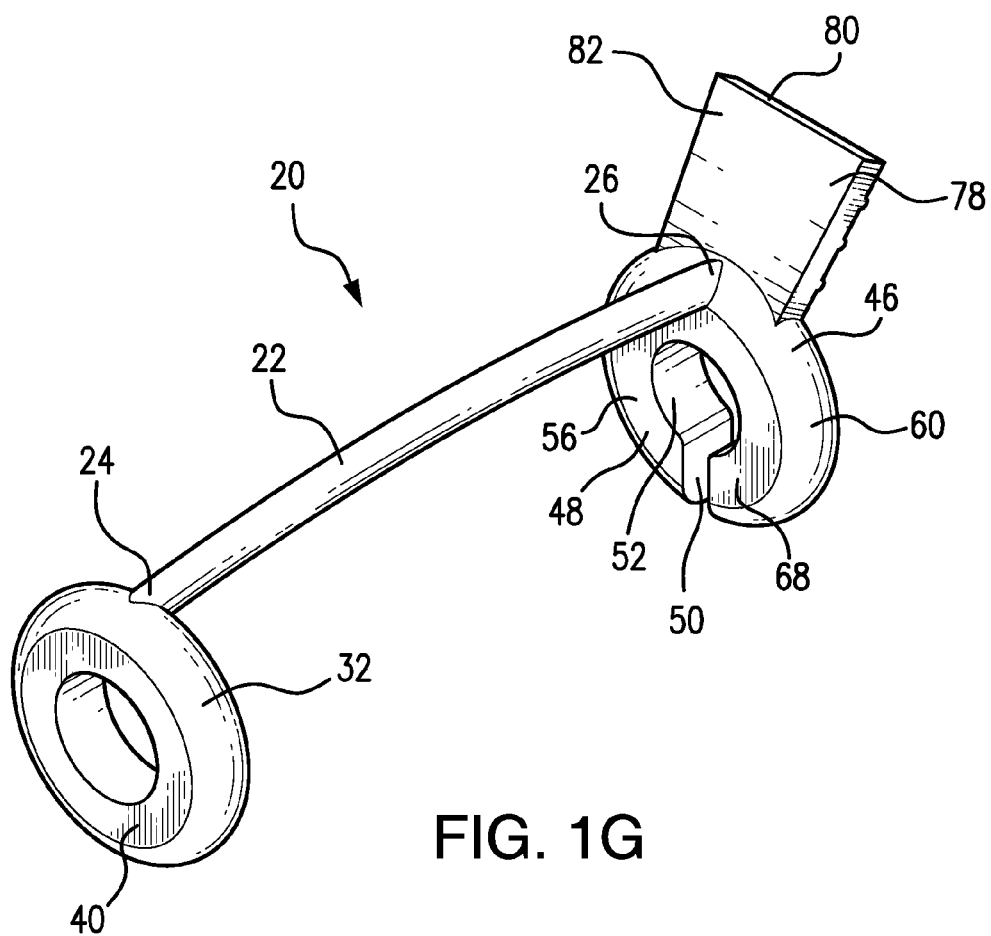
FIG. 1G is a back, top perspective view of the line separation protector shown in FIG. 1A.

FIG. 1E is a rear view of line separation protector 20. Lateral surface 82 of tab 78 is visible, as is arm 22, and anchor 32. Clasp 46, including gap 72, can be seen through anchor 32. FIG. 1F is a front view of line separation protector 20. Lateral surface 84 of tab 78 is visible, as is clasp 46 including first and second hooks 48 and 60, and anchor 32. FIG. 1G is a back, top perspective view of line separation protector 20, and shows the features of line separation protector 20 that are obscured in FIG. 1A. Anchor 32 is proximal to and intersects with first end 24 of arm 22. Outer lateral surface 40 of anchor 32 is visible in the foreground. Clasp 46 is proximal to and intersects with second end 26. Extending away from clasp 46 is tab 78 with first tab lateral surface 82 and tab edge 80 being visible. Inner lateral surface 56 of first hook 48 and inner lateral surface 68 of second hook 60 are shown facing anchor 32. Distal tip 50 of first hook 48 is also visible.

Figure 2:
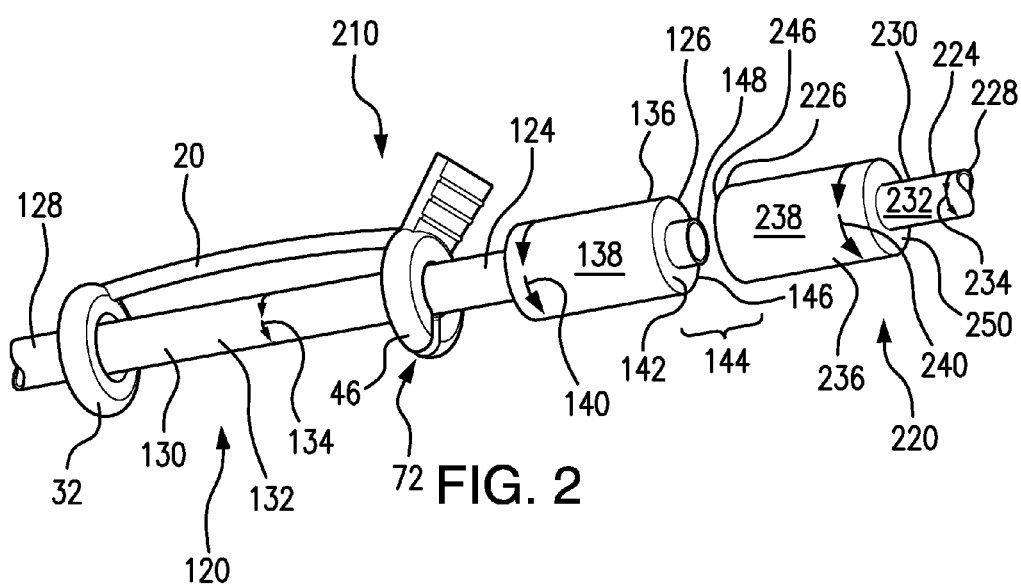
FIG. 2 is a perspective view of a line connection system including a line separation protector shown in a retracted position before application and showing first and second tubings in an unconnected, in-line configuration, in accordance with the present invention.

FIG. 2 is a perspective view of a line connection system 210 including the line separation protector (20) shown in FIGS. 1A-1G, in a retracted position. First and second tubing subsystems 120 and 220 are shown in an unconnected, but aligned configuration. First tubing subsystem 120 includes a first tubing 124. First tubing 124 includes a first end 126 and a second end 128 that is shown broken away. An intermediate section 130 is located between first and second ends 126 and 128. Intermediate section 130 includes an outer surface 132 that defines an intermediate section outer circumference 134 defined by a first outer diameter. A first connector section 136 is located adjacent to and intersecting intermediate section 130 and proximal to and intersecting with first end 126. Connector section 136 has an outer circumferential surface 138 defining an outer circumference 140. Outer circumference 140 is defined by the outer diameter of connector section 136, in this case, because connector section 136 has a circular, ring-shaped cross-section. Herein, while outer diameters and inner diameters are discussed, it is to be understood that for tubing and connectors having cross-sections that are not circular, ring-shaped, the anchor and clasp can have complementary shapes that also are not circular, ring-shaped. Regardless of cross-sectional shapes, the inner circumferential shapes of the anchor and clasp should accommodate the outer circumferential shapes of the portions of first tubing and second tubing, respectively, where they are engaged.

In FIG. 2, it can be seen that the outer circumference 140 of connector section 136 is larger than the outer circumference 134 of intermediate section 130. Connector section 136 also includes an outer lateral surface 142 at first end 126. Line separation protector 20 is mounted on first tubing subsystem 120 such that anchor 32 encircles intermediate section 130, as does clasp 46 with the exception of gap 72. The inner circumference of anchor 32 is smaller than the outer circumference 140 of connector section 136 and larger than or equal to outer circumference 134 of intermediate section 130. This relative sizing allows anchor 32 to encircle intermediate section 130 and move along the length of intermediate section 130, but helps prevent anchor 32 from sliding off first tubing 124 at first end 126.

Connector section 136 includes a first half 146 of a luer lock, which comprises male luer connector 148. Second tubing subsystem 220 includes a second tubing 224 having a first end 226, a second end 228, and an intermediate tubing section 230 located between first and second ends 226 and 228. Intermediate section 230 has an outer surface 232 defining an outer circumference 234. A connector section 236 is located adjacent intermediate section 230, proximal to and intersecting with first end 226. Connector section 236 has an outer circumferential surface 238 defining an outer circumference 240. Outer circumference 240 is larger than outer circumference 234 of immediate section 230. Connector section 236 also has an outer lateral surface 250 located adjacent and intersecting with intermediate section 230. Connector section 236 includes a second half 246 of a luer lock, which, together with complementary first half 146, constitutes a luer lock 144.

Figure 3A:
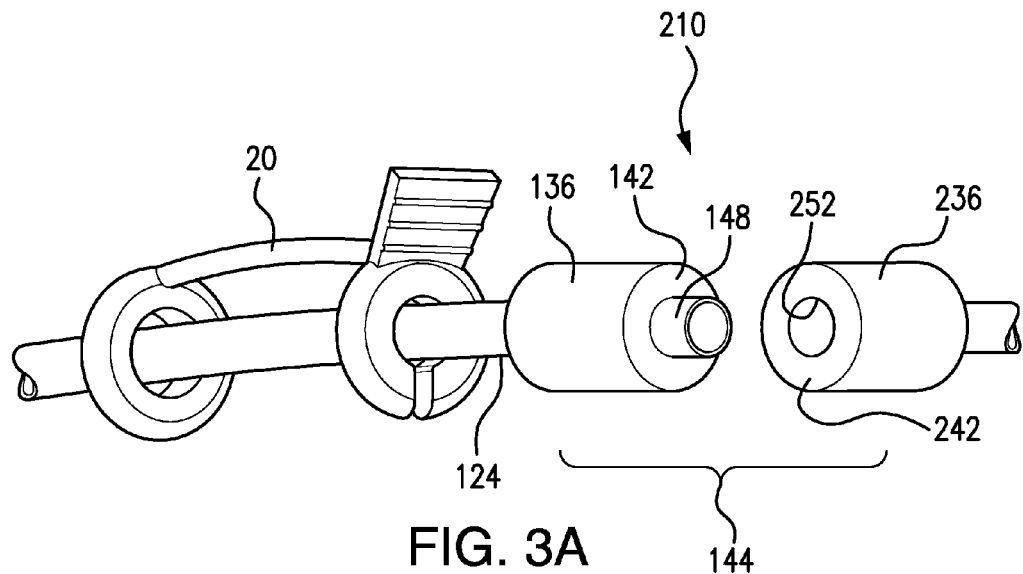
FIG. 3A is a front perspective view of the line connection system shown in FIG. 2, but with first and second tubings in an unconnected, angled configuration.

FIG. 3A is a front perspective view of line connection system 210 shown in FIG. 2, but with first and second tubing subsystems 120 and 220 shown in an unconnected, angled configuration. Although FIGS. 2-5 show a very basic male/female complementary set of locking features, more complicated locking features and connections can be provided to connect the two tubing subsystems together. Twist-and-look features, splines, ridges, protrusions, shoulders, and the like, can be provided to connect the two tubing subsystems together and/or prevent relative rotation between the two tubing subsystems.

Figure 3B:
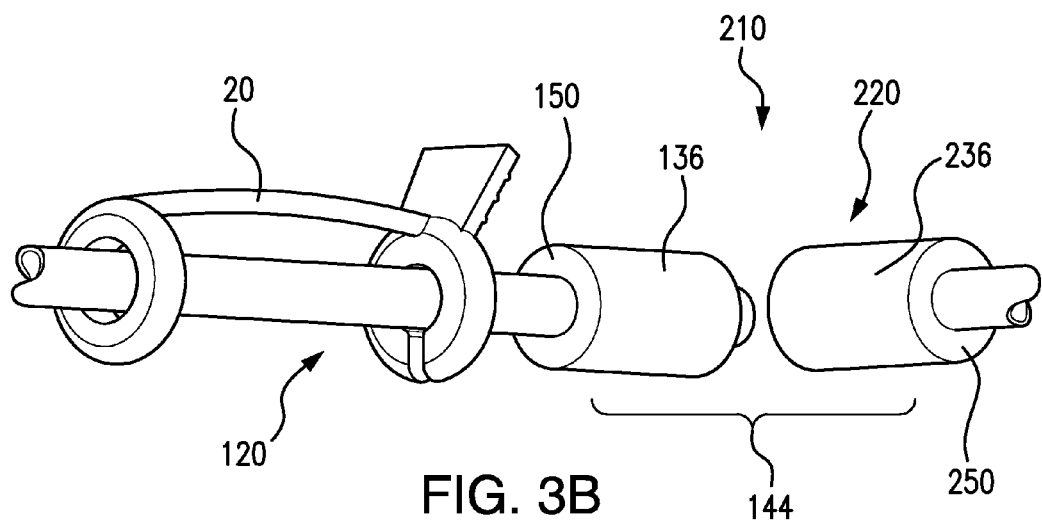
FIG. 3B is a rear perspective view of the line connection system shown in FIG. 3A.

In FIG. 3A line separation protector 20 remains in a retracted position connected to first tubing 124 at both the anchor and the clasp. First and second connector sections 136 and 236, respectively, are angled such that male luer connector 148 and female luer connector 252 of luer lock 144 are visible. An inner lateral surface 142 of connector section 136 is visible as is an inner lateral surface 242 of connector section 236. FIG. 3B is a rear perspective view of line connection system 210 shown in FIG. 3A and showing first and second tubing subsystems 120 and 220 that together constitute luer lock 144. An outer lateral surface 150 of connector section 136 is visible in FIG. 3B as is an outer lateral surface 250 of connector section 236.

FIG. 4 is a perspective view of line connection system 210 shown in FIGS. 2-3B, but with line separation protector 20 in a semi-detached position and first and second tubing subsystems 120 and 220 unconnected. Anchor 32 still encircles intermediate section 130, but clasp 46 has been disengaged such that arm 22 and tab 78 have been pulled away from intermediate section 130.

FIG. 5 is a perspective view of line connection system 210 shown in FIGS. 2-4, but with line separation protector 20 in an engaged position where it can protect first and second tubing subsystems 120 and 220 from separating from one another and disconnecting. In the connected configuration shown, a continuous connection is provided between intermediate section 130, connector section 136, connector section 236, and intermediate section 230. The inner lateral surface of anchor 32 is flush against the outer lateral surface of connector section 136 and the inner lateral surface of clasp 46 is flush against the outer lateral surface of connector section 236. Arm 22 is shown slightly bowed or arched away from first and second connector sections 136 and 236. The length of arm 22 can be configured such that no such bowing occurs, but either way, the length of arm 22 essentially equals the added lengths of first and second connector sections 136 and 236.

The present invention includes the following numbered aspects, embodiments, features, and methods in any order and/or in any combination:

1. A line separation protector comprising:
    an arm comprising a first end, a second end, an inner surface, and an outer surface, the arm extending in a first direction from the first end to the second end;
    a ring-shaped anchor connected to the first end and extending away from the arm in a direction that is substantially perpendicular to the first direction, the anchor having a through hold, an inner diameter, an outer diameter, an inner lateral surface, and an outer lateral surface;
    a ring-shaped, pliant clasp having a gap in the ring shape, the pliant clasp being connected to the second end and extending away from the arm in a direction that is substantially perpendicular to the first direction, the pliant clasp comprising a first hook extending from the arm and comprising a distal tip, a second hook extending from the arm and comprising a distal tip, and a through hole, wherein the first hook arcs toward the distal tip of the second hook, the second hook arcs toward the distal tip of the first hook, the distal tips of the first and second hooks are separated from one another by a gap, and the through hole is aligned with the through hole of the anchor; and
    a tab connected to the clasp, at a portion of the clasp opposite the gap, the tab extending away from the clasp, extending away from the arm, and configured to transfer pushing and pulling forces through the clasp and to the distal tips of the first and second hooks.

2. The line separation protector of any preceding or following embodiment/feature/aspect, wherein the first hook, the second hook, or both, are pliant.

3. The line separation protector of any preceding or following embodiment/feature/aspect, wherein the arm, the anchor, the tab, or any combination thereof, is pliant.

4. The line separation protector of any preceding or following embodiment/feature/aspect, wherein the line separation protector is formed from a pliant material and comprises a one-piece unitary construction.

5. The line separation protector of any preceding or following embodiment/feature/aspect, wherein the inner circumference of the anchor is larger than the inner circumference of the clasp.

6. The line separation protector of any preceding or following embodiment/feature/aspect, wherein the anchor has an inner lateral surface that is substantially parallel to inner lateral surfaces of the first and second hooks.

7. The line separation protector of any preceding or following embodiment/feature/aspect, wherein the gap has an arc length that is less than about 90°.

8. The line separation protector of any preceding or following embodiment/feature/aspect, wherein the gap has an arc length that is less than about 30°.

9. A tubing subsystem comprising:
    a first tubing having a first end, a second end, an intermediate section between the first and second ends, and a first connector section adjacent to and intersecting the intermediate section proximal to the first end, the intermediate section having an outer circumference, the first connector section having an outer circumference that is larger than the outer circumference of the intermediate section, and the first connector section having an outer lateral surface that intersects with the intermediate section; and
    the line separation protector of any preceding or following embodiment/feature/aspect,
    wherein intermediate section passes though the anchor such that the anchor encircles the intermediate section, an inner circumference of the anchor is smaller than the outer circumference of the first connector section, and the inner circumference of the anchor is larger than or equal to the outer circumstance of the intermediate section.

10. The tubing subsystem of any preceding or following embodiment/feature/aspect, wherein the inner circumference of the anchor is larger than the outer circumference of the immediate section.

11. The tubing subsystem of any preceding or following embodiment/feature/aspect, wherein the connector section comprises a first half of a luer lock.

12. The tubing subsystem of any preceding or following embodiment/feature/aspect, wherein the first half of the luer lock comprises a male luer connector.

13. A disposable blood tubing set comprising the tubing subsystem of any preceding or following embodiment/feature/aspect, wherein the first tubing comprises a blood line.

14. A line connection system comprising:
    the tubing subsystem of any preceding or following embodiment/feature/aspect; and
    a second tubing, the second tubing having a first end, a second end, an intermediate section between the first and second ends, and a second connector section adjacent to and intersecting the intermediate section of the second tubing proximal to the first end of the second tubing, the second connector section having an outer circumference that is larger than an outer circumference of the intermediate section of the second tubing, and the second connector section having an outer lateral surface intersecting the intermediate section of the second tubing;
    wherein the clasp has an inner circumference that is smaller than the outer circumference of the second connector section, and the first and second connector sections are configured to join together to enable fluid communication between the first and second tubings.

15. The line connection system of any preceding or following embodiment/feature/aspect, wherein the first and second tubings are connected to each other and the clasp substantially encircles the intermediate section of the second tubing.

16. The line connection system of any preceding or following embodiment/feature/aspect, wherein the pliant clasp completely surrounds the intermediate section of the second tubing except at the gap.

17. The line connection system of any preceding or following embodiment/feature/aspect, wherein the inner circumference of the clasp is larger than or equal to the outer circumference of the intermediate section of the second tubing.

18. The line connection system of any preceding or following embodiment/feature/aspect, wherein the arm has an arm length, the anchor has an inner lateral surface, the first and second hooks each have an inner lateral surface, the arm length is the distance between the inner lateral surface of the anchor and the inner lateral surfaces of the first and second hooks, the first connector section has a first length, the second connector section has a second length, the first and second connector sections, when joined together, define a connector length that is equal to the sum of the first and second connector tubing lengths, and the arm length is longer than or equal to the connector length.

19. The line connection system of any preceding or following embodiment/feature/aspect, wherein the arm length is equal to the connector length.

20. The line connection system of any preceding or following embodiment/feature/aspect, wherein the inner lateral surface of the anchor is in contact with the outer lateral surface of the first connector section, and the inner lateral surfaces of the first and second hooks are in contact with the outer lateral surface of the second connector section.

21. The line connection system of any preceding or following embodiment/feature/aspect, wherein the arm has an inner surface that is in contact with the first and second connector sections.

22. The line connection system of any preceding or following embodiment/feature/aspect, wherein the second connector section comprises a second half of a luer lock.

23. The line connection system of any preceding or following embodiment/feature/aspect, wherein the second half of the luer lock comprises a female luer connector.

24. The line connection system of any preceding or following embodiment/feature/aspect, wherein the second tubing comprises a catheter line, a needle access line, or both.

25. A method of protecting the line connection system of any preceding or following embodiment/feature/aspect, the method comprising engaging the intermediate section of the second tubing with the pliant clasp to form a protected line connection system.

26. The method of any preceding or following method/embodiment/feature/aspect, further comprising sliding the anchor along the intermediate section of the first tubing until the inner lateral surface of the anchor contacts the outer lateral surface of the first connector section, and then engaging the intermediate section of the second tubing with the pliant clasp.

27. The method of any preceding or following method/embodiment/feature/aspect, further comprising joining the first and second connector sections together to enable fluid communication between the first and second tubings, prior to the engaging.

28. The method of any preceding or following method/embodiment/feature/aspect, further comprising disengaging the pliant clasp from the intermediate section of the second tubing.

29. The method of any preceding method/embodiment/feature/aspect, wherein the engaging, the disengaging, or both, comprises gripping the tab.

The entire contents of all references cited in this disclosure are incorporated herein in their entireties, by reference. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A line separation protector comprising:
an arm comprising a first end, a second end, an inner surface, and an outer surface, the arm extending in a first direction from the first end to the second end;
a ring-shaped anchor connected to the first end and extending away from the arm in a direction that is substantially perpendicular to the first direction, the anchor having a through hole, an inner diameter, an outer diameter, an inner lateral surface, and an outer lateral surface, the ring-shaped anchor comprising a closed ring configured to encircle a length of tubing when such a length of tubing is inserted into the through hole;
a ring-shaped, pliant clasp having a gap in the ring shape, the pliant clasp being connected to the second end and extending away from the arm in a direction that is substantially perpendicular to the first direction, the pliant clasp comprising a first hook extending from the arm and comprising a distal tip, a second hook extending from the arm and comprising a distal tip, and a through hole, wherein the first hook arcs toward the distal tip of the second hook, the second hook arcs toward the distal tip of the first hook, the distal tips of the first and second hooks are separated from one another by a gap, and the through hole is aligned with the through hole of the anchor; and
a tab connected to the clasp, at a portion of the clasp opposite the gap, the tab extending away from the clasp, extending away from the arm, and configured to transfer pushing and pulling forces through the clasp and to the distal tips of the first and second hooks.

2. The line separation protector of claim 1, wherein the first hook, the second hook, or both, are pliant.

3. The line separation protector of claim 1, wherein the arm, the anchor, the tab, or any combination thereof, is pliant.

4. The line separation protector of claim 1, wherein the line separation protector is formed from a pliant material and comprises a one-piece unitary construction.

5. The line separation protector of claim 1, wherein the inner circumference of the anchor is larger than the inner circumference of the clasp.

6. The line separation protector of claim 1, wherein the anchor has an inner lateral surface that is substantially parallel to inner lateral surfaces of the first and second hooks.

7. The line separation protector of claim 1, wherein the gap has an arc length of less than about 30°.

8. A tubing subsystem comprising:
a first tubing having a first end, a second end, an intermediate section between the first and second ends, and a first connector section adjacent to and intersecting the intermediate section proximal to the first end, the intermediate section having an outer circumference, the first connector section having an outer circumference that is larger than the outer circumference of the intermediate section, and the first connector section having an outer lateral surface that intersects with the intermediate section; and
the line separation protector of claim 1,
wherein intermediate section passes though the anchor such that the anchor encircles the intermediate section, an inner circumference of the anchor is smaller than the outer circumference of the first connector section, and the inner circumference of the anchor is larger than or equal to the outer circumference of the intermediate section.

9. The tubing subsystem of claim 8, wherein the inner circumference of the anchor is larger than the outer circumference of the intermediate section.

10. A line connection system comprising:
the tubing subsystem of claim 8; and
a second tubing, the second tubing having a first end, a second end, an intermediate section between the first and second ends, and a second connector section adjacent to and intersecting the intermediate section of the second tubing proximal to the first end of the second tubing, the second connector section having an outer circumference that is larger than an outer circumference of the intermediate section of the second tubing, and the second connector section having an outer lateral surface intersecting the intermediate section of the second tubing;
wherein the clasp has an inner circumference that is smaller than the outer circumference of the second connector section, and the first and second connector sections are configured to join together to enable fluid communication between the first and second tubings.

11. The line connection system of claim 10, wherein the first and second tubings are connected to each other and the clasp substantially encircles the intermediate section of the second tubing.

12. The line connection system of claim 10, wherein the arm has an arm length, the anchor has an inner lateral surface, the first and second hooks each have an inner lateral surface, the arm length is the distance between the inner lateral surface of the anchor and the inner lateral surfaces of the first and second hooks, the first connector section has a first length, the second connector section has a second length, the first and second connector sections, when joined together, define a connector length that is equal to the sum of the first and second connector tubing lengths, and the arm length is longer than or equal to the connector length.

13. The line connection system of claim 10, wherein the inner lateral surface of the anchor is in contact with the outer lateral surface of the first connector section, and the inner lateral surfaces of the first and second hooks are in contact with the outer lateral surface of the second connector section.

14. The line connection system of claim 10, wherein the second tubing comprises a catheter line, a needle access line, or both.

15. A method of protecting the line connection system of claim 10, the method comprising engaging the intermediate section of the second tubing with the pliant clasp to form a protected line connection system.

16. The method of claim 15, further comprising sliding the anchor along the intermediate section of the first tubing until the inner lateral surface of the anchor contacts the outer lateral surface of the first connector section, and then engaging the intermediate section of the second tubing with the pliant clasp.

17. The method of claim 15, further comprising joining the first and second connector sections together to enable fluid communication between the first and second tubings, prior to the engaging.

18. The method of claim 17, further comprising disengaging the pliant clasp from the intermediate section of the second tubing.

19. The method of claim 18, wherein the engaging, the disengaging, or both, comprises gripping the tab.

20. A line separation protector comprising:
an arm comprising a first end, a second end, an inner surface, and an outer surface, the arm extending in a first direction from the first end to the second end;
a ring-shaped anchor connected to the first end and extending away from the arm in a direction that is substantially perpendicular to the first direction, the anchor having a through hole, an inner diameter, an outer diameter, an inner lateral surface, and an outer lateral surface;
a ring-shaped, pliant clasp having a gap in the ring shape, the pliant clasp being connected to the second end and extending away from the arm in a direction that is substantially perpendicular to the first direction, the pliant clasp comprising a first hook extending from the arm and comprising a distal tip, a second hook extending from the arm and comprising a distal tip, and a through hole, wherein the first hook arcs toward the distal tip of the second hook, the second hook arcs toward the distal tip of the first hook, the distal tips of the first and second hooks are separated from one another by a gap, and the through hole is aligned with the through hole of the anchor; and
a tab connected to the clasp, at a portion of the clasp opposite the gap, the tab extending away from the clasp, extending away from the arm, and configured to transfer pushing and pulling forces through the clasp and to the distal tips of the first and second hooks,
wherein the arm is a single arm and the only arm connecting the ring-shaped anchor to the ring-shaped, pliant clasp.

21. A line separation protector comprising:
an arm comprising a first end, a second end, an inner surface, and an outer surface, the arm extending in a first direction from the first end to the second end;
a ring-shaped anchor connected to the first end and extending away from the arm in a direction that is substantially perpendicular to the first direction, the anchor having a through hole, an inner diameter, an outer diameter, an inner lateral surface, and an outer lateral surface;
a ring-shaped, pliant clasp having a gap in the ring shape, the pliant clasp being connected to the second end and extending away from the arm in a direction that is substantially perpendicular to the first direction, the pliant clasp comprising a first hook extending from the arm and comprising a distal tip, a second hook extending from the arm and comprising a distal tip, and a through hole, wherein the first hook arcs toward the distal tip of the second hook, the second hook arcs toward the distal tip of the first hook, the distal tips of the first and second hooks are separated from one another by a gap, and the through hole is aligned with the through hole of the anchor; and
a tab connected to the clasp, at a portion of the clasp opposite the gap, the tab extending away from the clasp, extending away from the arm, and configured to transfer pushing and pulling forces through the clasp and to the distal tips of the first and second hooks,
wherein the second end of the arm intersects with and is connected to the ring-shaped, pliant clasp at a location on the ring shape, which is opposite the gap in the ring shape.

* * * * *